United States Patent
Makrigiorgos

(10) Patent No.: US 8,623,603 B2
(45) Date of Patent: Jan. 7, 2014

(54) FULL COLD-PCR ENRICHMENT WITH REFERENCE BLOCKING SEQUENCE

(75) Inventor: Gerassimos Makrigiorgos, Chestnut Hill, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 214 days.

(21) Appl. No.: 13/042,549

(22) Filed: Mar. 8, 2011

(65) Prior Publication Data

US 2011/0217714 A1    Sep. 8, 2011

Related U.S. Application Data

(60) Provisional application No. 61/311,642, filed on Mar. 8, 2010.

(51) Int. Cl.
*C12Q 1/68* (2006.01)
*C12P 19/34* (2006.01)

(52) U.S. Cl.
USPC .................................... 435/6.12; 435/91.2

(58) Field of Classification Search
USPC .............................. 435/6.12, 91.2
See application file for complete search history.

(56) References Cited

U.S. PATENT DOCUMENTS 5,849,497 A * 12/1998 Steinman ...................... 435/6.11
2007/0020672 A1* 1/2007 Wittwer et al. ................... 435/6

FOREIGN PATENT DOCUMENTS

| WO | WO2007106534 | * | 9/2007 | ........... | C12Q 1/68 |
| WO | 2009/017784 | | 2/2009 | | |
| WO | 2009/019008 | | 2/2009 | | |
| WO | WO2009019008 | * | 2/2009 | ........... | C12Q 1/68 |
| WO | WO2009017784 | * | 2/2010 | ........... | C12Q 1/68 |

OTHER PUBLICATIONS

Dominguez PL, Kolodney MS. Wild-type blocking polymerase chain reaction for detection of single nucleotide minority mutations from clinical specimens. Oncogene. 2005. 24(45):6830-4.*
Li J, Wang L, Mamon H, Kulke MH, Berbeco R, Makrigiorgos GM. Replacing PCR with COLD-PCR enriches variant DNA sequences and redefines the sensitivity of genetic testing. Nat Med. 2008. 14(5):579-84.*
International Preliminary Report on patentability (IPRP) of PCT/US2011/027473 for WO2011-112534 filed on Nov. 9, 2012.*
International Preliminary Report on patentability (IPRP) of PCT/US2008/009248 for WO2009-017784 filed on Feb. 2, 2010.*
International Preliminary Report on patentability (IPRP) of PCT/EP2008/006476 for WO2009-019008 filed on Sep. 2, 2010.*
Amicarelli G, Shehi E, Makrigiorgos GM, Adlerstein D. FLAG assay as a novel method for real-time signal generation during PCR: application to detection and genotyping of KRAS codon 12 mutations. Nucleic Acids Res. 2007;35(19):e131. Epub Oct. 11, 2007.*
Dabritz J, Hanfler J, Preston R, Stieler J, Oettle H. Detection of Ki-ras mutations in tissue and plasma samples of patients with pancreatic cancer using PNA-mediated PCR clamping and hybridisation probes. Br J Cancer 2005; 92:405-12.*
Li (b) et al.. Replacing PCR with COLD-PCR enriches variant DNA sequences and redefines the sensitivity of genetic testing. Nat Med. May 2008;14(5):579-84. Epub Apr. 13, 2008.*
Li (c) et al. Two-round coamplification at lower denaturation temperature-PCR(COLD-PCR)-based sanger sequencing identifies a novel spectrum of low-level mutations in lung adenocarcinoma. Hum Mutat. Nov. 2009;30(11):1583-90.*
Luthra R, Zuo Z. COLD-PCR finds hot application in mutation analysis. Clin Chem. Dec. 2009; 55(12):2077-8. Epub Oct. 15, 2009.*
Milbury (a) et al. COLD-PCR-enhanced high-resolution melting enables rapid and selective identification of low-level unknown mutations. Clin Chem. Dec. 2009; 55(12):2130-43. Epub Oct. 8, 2009.*
Milbury (b) et al. PCR-based methods for the enrichment of minority alleles and mutations. Clin Chem. Apr. 2009; 55(4):632-40. Epub Feb. 6, 2009. Review.*
Oldenburg RP, Liu MS, Kolodney MS. Selective amplification of rare mutations using locked nucleic acid oligonucleotides that competitively inhibit primer binding to wild-type DNA. J Invest Dermatol 2008;128:398-402.*
Li Jin et al.: Coamplification at Lower Denaturation Temperature-PCR Increases Mutation-Detection Selectivity of TaqMan-Base Real-Time PCT, Clinical Chemistry, vol. 55, No. 4, Apr. 2009, pp. 748-756.
Li Jin et al.: COLD-PCT: a new platform for highly improved mutation detection in cancer and genetic testing, Biochmeical Society Transactions, Portland PRess Ltd., GB, vol. 37, No. Pt. 2, Apr. 1, 2009, pp. 427-432.
Dominguez Patrick L. et al.: Wild-type blocking polymerase chain reaction for detection of single nucleotide minority mutations from clinical specimens, Oncogene, Nature Publishing Group, GB, vol. 24, No. 45, Oct. 1, 2005, pp. 6830-6834.
Milbury, Coren A. et al.: Ice-COLD-PCT enables rapid amplification and robust enrichment for low-abundance unknown DNA mutations., Nucleic Acids Research, Jan. 1, 2011, LNKD-PUBMED:20937629, vol. 39, No. 1, E2, Oct. 11, 2010, pp. 1-10.

* cited by examiner

*Primary Examiner* — Kenneth R. Horlick
*Assistant Examiner* — Olayinka Oyeyemi
(74) *Attorney, Agent, or Firm* — Andrus, Sceales, Starke & Sawall, LLP

(57) ABSTRACT

The present invention is directed to methods, compositions and software for enriching low abundance alleles in a sample. It is directed in particular to the use of an excess amount of reference blocking sequence in an amplification reaction mixture in order to improve the enrichment efficiency, and reduce cycle time, of full COLD-PCR.

23 Claims, 8 Drawing Sheets

A     PRINCIPLE OF FULL COLD PCR
(Co-amplification at Lower Denaturation temperature)

AMPLIFY SELECTIVELY THE MUTATION-CONTAINING SEQUENCES

B     COLD-PCR

(simplex, multiplex, or common linker-mediated CO.L.D-PCR)

FIGURE 3

87bp amplicon, RBS60

5'- TGGTAATCTACTGGGACGGAACAGCTTTGAGGTGCGTGTTTGTGCCTGTCCTGGGAGAGACCGGGCACAGAGGAAGAGAATCTCCGC -3'
       3'-PO₄- ━━━━━━━━━━━━━━━━━━━━━ 5' RBS60

3'- ACCATTAGATGACCCTGCCTTGTCGAAACTCCACGCACAAACACGGACGAGGACCCTCTCTGGCCGGTGTCTCCTTCTCTCTTAGAGGCG -5'

US 8,623,603 B2

SEQUENCE LISTING

<160> NUMBER OF SEQ ID NOS: 13

<210> SEQ ID NO 1
<211> LENGTH: 20

-continued

```
<212> TYPE: DNA
<213> ORGANISM: Artificial
<220> FEATURE:
<223> OTHER INFORMATION: Oligonucleotide primer for polymerase chain
      amplification of human p53 gene

<400> SEQUENCE: 1
gcttctcttt tcctatcctg                                              20

<210> SEQ ID NO 2
<211> LENGTH: 18
<212> TYPE: DNA
<213> ORGANISM: Artificial
<220> FEATURE:
<223> OTHER INFORMATION: Oligonucleotide primer for polymerase chain
      amplification of human p53 gene

<400> SEQUENCE: 2
cttacctcgc ttagtgct                                                18

<210> SEQ ID NO 3
<211> LENGTH: 18
<212> TYPE: DNA
<213> ORGANISM: Artificial
<220> FEATURE:
<223> OTHER INFORMATION: Oligonucleotide primer for polymerase chain
      amplification of human p53 gene

<400> SEQUENCE: 3
tggtaatcta ctgggacg                                                18

<210> SEQ ID NO 4
<211> LENGTH: 18
<212> TYPE: DNA
<213> ORGANISM: Artificial
<220> FEATURE:
<223> OTHER INFORMATION: Oligonucleotide primer for polymerase chain
      amplification of human p53 gene

<400> SEQUENCE: 4
cggagattct cttcctct                                                18

<210> SEQ ID NO 5
<211> LENGTH: 48
<212> TYPE: DNA
<213> ORGANISM: Artificial
<220> FEATURE:
<223> OTHER INFORMATION: Oligonucleotide primer for polymerase chain
      amplification of human p53 gene

<400> SEQUENCE: 5
tttttttttt tttttttttt tttttttttt tggtaatcta ctgggacg               48

<210> SEQ ID NO 6
<211> LENGTH: 15
<212> TYPE: DNA
<213> ORGANISM: Artificial
<220> FEATURE:
<223> OTHER INFORMATION: Oligonucleotide primer for polymerase chain
      amplification of human p53 gene

<400> SEQUENCE: 6
ggacggaaca gcttt                                                   15

<210> SEQ ID NO 7
<211> LENGTH: 15
<212> TYPE: DNA
<213> ORGANISM: Artificial
```

-continued

```
<220> FEATURE:
<223> OTHER INFORMATION: Oligonucleotide primer for polymerase chain
      amplification of human p53 gene

<400> SEQUENCE: 7
ctggccgcgt gtctc                                                    15

<210> SEQ ID NO 8
<211> LENGTH: 60
<212> TYPE: DNA
<213> ORGANISM: Artificial
<220> FEATURE:
<223> OTHER INFORMATION: Oligonucleotide that hybridizes to human p53
      gene

<400> SEQUENCE: 8
ctctgtgcgc cggtctctcc caggacaggc acaaacacgc acctcaaagc tgttccgtcc    60

<210> SEQ ID NO 9
<211> LENGTH: 20
<212> TYPE: DNA
<213> ORGANISM: Artificial
<220> FEATURE:
<223> OTHER INFORMATION: Oligonucleotide primer for polymerase chain
      amplification of human p53 gene

<400> SEQUENCE: 9
gcttctcttt tcctatcctg                                               20

<210> SEQ ID NO 10
<211> LENGTH: 18
<212> TYPE: DNA
<213> ORGANISM: Artificial
<220> FEATURE:
<223> OTHER INFORMATION: Oligonucleotide primer for polymerase chain
      amplification of human p53 gene

<400> SEQUENCE: 10
cttacctcgc ttagtgct                                                 18

<210> SEQ ID NO 11
<211> LENGTH: 18
<212> TYPE: DNA
<213> ORGANISM: Artificial
<220> FEATURE:
<223> OTHER INFORMATION: Oligonucleotide primer for polymerase chain
      amplification of human p53 gene

<400> SEQUENCE: 11
ttgcttctct tttcctat                                                 18

<210> SEQ ID NO 12
<211> LENGTH: 60
<212> TYPE: DNA
<213> ORGANISM: Artificial
<220> FEATURE:
<223> OTHER INFORMATION: Oligonucleotide primer for polymerase chain
      amplification of human p53 gene

<400> SEQUENCE: 12
tttttttttt tttttttttt tttttttttt tttttttttt ttgcttctct tttcctatcc   60

<210> SEQ ID NO 13
<211> LENGTH: 90
<212> TYPE: DNA
<213> ORGANISM: Artificial
```

-continued

```
<220> FEATURE:
<223> OTHER INFORMATION: Oligonucleotide that hybridizes to human p53
      gene

<400> SEQUENCE: 13
cttcctctgt gcgccggtct ctcccaggac aggcacaaac acgcacctca aagctgttcc    60
gtcccagtag attaccacta ctcaggatag                                     90
```

FULL COLD-PCR ENRICHMENT WITH REFERENCE BLOCKING SEQUENCE

FIELD OF THE INVENTION

The invention pertains to improvements to the amplification and enrichment of low prevalence target sequences, e.g. mutations, in nucleic acid samples. In particular, the invention pertains to the use of reference blocking sequences during full COLD-PCR (CO-amplification at Lower Denaturation temperature).

BACKGROUND OF THE INVENTION

A commonly encountered situation in genetic analysis entails the need to identify a low percent of variant DNA sequences ('target sequences') in the presence of a large excess of non-variant sequences ('reference sequences'). Examples for such situations include: (a) identification and sequencing of a few mutated alleles in the presence of a large excess of normal alleles; (b) identification of a few methylated alleles in the presence of a large excess of unmethylated alleles (or vice versa) in epigenetic analysis; (c) detection of low levels of heteroplasmy in mitochondrial DNA; (d) detection of drug-resistant quasi-species in viral infections and (e) identification of tumor-circulating DNA in blood of cancer patients (where people are suspected of having cancer, to track the success of cancer treatment or to detect relapse) in the presence of a large excess of wild-type alleles.

The inventor of the present application has previously described COLD-PCR methods for enriching the concentration of low abundance alleles in a sample PCR reaction mixture; see published patent PCT application entitled "Enrichment of a Target Sequence", International Application No. PCT/US2008/009248, now U.S. Ser. No. 12/671,295, by Gerassimos Makrigiorgos and assigned to the assignee of the present invention. The described COLD-PCR enrichment methods are based on a modified nucleic acid amplification protocol which incubates the reaction mixture at a critical denaturing temperature "$T_c$". The prior patent application discloses two formats of COLD-PCR, namely full COLD-PCR and fast COLD-PCR.

In full COLD-PCR, the reaction mixture is subjected to a first denaturation temperature (e.g., 94° C.) which is chosen well above the melting temperature for the reference (e.g., wild-type) and target (e.g., mutant) sequences similar to conventional PCR. Then, the mixture is cooled slowly to facilitate the formation of reference-target heteroduplexes by hybridization. Steady lowering of the temperature in a controlled manner from 94° C. to 70° C. over an 8 minute time period is typical to assure proper hybridization. Alternatively, the temperature is rapidly lowered to 70° C. and retained at this temperature for 8 min to assure proper hybridization. Once cooled, the reaction mixture contains not only reference-target heteroduplexes but also reference-reference homoduplexes (and to a lesser extent target-target homoduplexes). When the target sequence and reference sequence cross hybridize, minor sequence differences of one or more single nucleotide mismatches or insertions or deletions anywhere along a short (e.g., <200 bp) double stranded DNA sequence will generate a small but predictable change in the melting temperature ($T_m$) for that sequence (Lipsky, R. H., et al. (2001) Clin Chem, 47, 635-644; Liew, M., et al. (2004) Clin Chem, 50, 1156-1164). Depending on the exact sequence context and position of the mismatch, melting temperature changes of 0.1-20° C., are contemplated. Full COLD-PCR, as described in the above referred patent application, is premised on the difference in melting temperature between the double stranded reference sequence and the hybridized reference-target heteroduplexes. After cooling down to form reference-target heteroduplexes, the reaction mixture is incubated at a critical denaturing temperature ($T_c$), which is chosen to be less than the melting temperature for the double stranded reference sequence and higher than the lower melting temperature of the reference-target heteroduplexes, thereby preferentially denaturing the cross hybridized target-reference heteroduplexes over the reference-reference homoduplexes.

The critical denaturing temperature ($T_c$) is a temperature below which PCR efficiency drops abruptly for the reference nucleic acid sequence (yet sufficient to facilitate denaturation of the reference-target heteroduplexes). For example, a 167 bp p53 sequence amplifies well if the PCR denaturing temperature is set at 87° C., amplifies modestly at 86.5° C. and yields no detectable product if PCR denaturation is set at 86° C. or less. Therefore, in this example $T_c$~86.5° C. After intermediate incubation at the critical denaturing temperature ($T_c$), the primers are annealed to the denatured target and reference strands from the denatured heteroduplexes and extended by a polymerase, thus enriching the concentration of the target sequence relative to the reference sequence. One of the advantages of full COLD-PCR is that the same primer pair is used for both target and reference sequences.

Fast COLD-PCR, as described in the above referred patent application, is premised on there being a difference in melting temperature between the double stranded reference sequence (e.g., wild-type sequence) and the double stranded target sequence (e.g., mutant sequence). In particular, the melting temperature of the target sequence must be lower than the reference sequence. The critical denaturing temperature ($T_c$) in fast COLD-PCR is a temperature below which PCR efficiency drops abruptly for the double stranded reference nucleic acid sequence, yet is still sufficient to facilitate denaturation of the double stranded target sequence. During the fast COLD-PCR enrichment cycle, the reaction mixture is not subjected to denaturation at a temperature (e.g., 94° C.) above the melting temperature of the reference sequence as in the first step of the full COLD-PCR cycle. Rather, the reaction mixture is incubated at a critical denaturing temperature (e.g., $T_c$=83.5° C.), which is chosen either (a) to be less than the melting temperature for the double stranded reference sequence and higher than the lower melting temperature of the double stranded target sequence, or; (b) to be lower than the $T_m$ of both reference and target sequences, whilst still creating a differential between the degree of denaturation of reference and target sequences. After incubation at the critical denaturing temperature ($T_c$), the primers are annealed to the denatured target strands and extended by a polymerase, thus enriching the concentration of the target sequence relative to the reference sequence. Again, the same primer pair is used for both target and reference sequences.

Enrichment via full COLD-PCR has been found to be relatively inefficient, and time consuming, compared to enrichment via fast COLD-PCR. However, the use of fast COLD-PCR is limited to applications in which the melting temperature of the double stranded target sequence is suitably less than the melting temperature for the double stranded reference sequence. For example, mutations will not be detectable in sequencing data for a sample with a low abundance of mutant sequences that has been subjected to fast COLD-PCR if the melting temperature of the mutant sequence is the same or higher than the melting temperature of the wild-type sequence. Therefore, it is desired to improve the efficacy and rate of the full COLD-PCR cycle.

It is believed that the relative inefficiency of full COLD-PCR is due primarily to the paucity of heteroduplexes formed particularly during the early cycles of full COLD-PCR. Even if slow cool down during the hybridization step is optimized (e.g., steadily cool down for 8 minutes from 94° C. to 70° C.), the very low concentration of target (e.g. mutant) strands especially during early cycles reduces the ability to form heteroduplexes. Increasing the time for hybridization cool down is not desired, and in any event has not been found to be particularly effective to improve enrichment. Another reason that full COLD-PCR may be relatively less efficient than fast COLD-PCR is that the amplicons during later cycles of full COLD-PCR have a propensity to reform their homoduplexes rather than form heteroduplexes.

One object of the present invention is to improve the efficiency of heteroduplex formation in the early cycles of full COLD-PCR. Another object is to decrease the overall cycle time for full COLD-PCR.

SUMMARY OF THE INVENTION

The present invention is directed to methods for enriching low abundance alleles in a sample, and is directed in particular to the use of an excess amount of reference blocking sequence in the reaction mixture in order to improve the efficiency, and reduce cycle time, of full COLD-PCR.

The present invention involves a modification to the COLD-PCR methods described in connection with FIGS. 1 and 2 of the above referred patent application, "Enrichment of a Target Sequence", International Application No. PCT/US2008/009248, now U.S. Ser. No. 12/671,295, by Gerassimos Makrigiorgos and assigned to the assignee of the present invention, and which is herby incorporated herein by reference. More specifically, in accordance with the invention, an engineered reference blocking sequence (e.g., a single stranded oligonucleotide) is added in excess to the reaction mixture prior to subjecting the reaction mixture to thermocycling per a modified, full COLD-PCR protocol.

The modified, full COLD-PCR method involves the preparation of an amplification reaction mixture containing a nucleic acid sample. The nucleic acid sample will have a reference sequence, such as a wild-type sequence, and will also be suspected of containing one or more target sequences, such as one or more mutant sequences. As mentioned, the purpose of the invention is to enrich the concentration of the target sequence, and therefore in most circumstances, the method will be used when the target sequence, if present, is in low abundance. The target sequence in accordance with the invention is at least 50% homologous to the reference sequence, although the method is especially well suited to enrich a mutant allele containing about 1 to 10 nucleotide sequence changes. The target sequence is amplifiable via PCR with the same pair of primers as those used for the reference sequence. As mentioned, the invention involves the presence of a reference blocking sequence in the reaction mixture at an excess concentration level. The reference blocking sequence is a nucleic acid sequence complementary with at least a portion of one of the strands of the reference sequence between its primer sites, or partly overlapping the primer sites. The reference blocking sequence added to the reaction mixture is desirably single stranded (but can also be double stranded inasmuch as the initial denaturing step will result in denatured, single stranded reference blocking sequences).

In accordance with the full COLD-PCR protocol, the reaction mixture is subjected to a first denaturing temperature, e.g. 95° C., which is above the melting temperature ($T_m$) of the reference sequence and also the target sequence, and results in denatured strands of the reference sequence and the target sequence. The reaction mixture is cooled to promote hybridization, for example to about 70° C. Since the cooling down occurs in the presence of an excess amount of reference blocking sequences, the reference blocking sequences preferentially hybridize with the complementary strand of the reference sequence, and also the complementary strand of the target sequence. For example, assuming that single stranded reference blocking sequence is added in excess at the beginning of the process, the reaction mixture at this point in the process will contains heteroduplexes of the reference blocking sequences and the complementary reference (e.g., wild-type) strand and heteroduplexes of the reference blocking sequences and the target (e.g. mutant) strands. The reaction mixture at this point also contains the denatured negative strands for the reference and target sequences. The formed heteroduplexes present in the modified full COLD-PCR cycle are fundamentally different from the reference-target heteroduplexes formed in the full COLD-PCR protocol described in the above referenced patent application. Supplying an excess amount of reference blocking sequence promotes faster hybridization (e.g., about 30 seconds) than in the prior full COLD-PCR protocol (e.g., about 8 minutes). In a preferred embodiment of the present invention, the cool down hybridization step is less than one minute in duration.

The reaction mixture is then subjected to a critical temperature (e.g., $T_c$=84.5° C.) which is sufficient to permit preferential denaturation of the target strands from the reference blocking sequence. The critical temperature ($T_c$) is selected so that duplexes of the reference blocking strands and the complementary reference strands remain substantially undenatured when the reaction mixture is incubated at $T_c$ yet duplexes of the reference blocking strands and the target strands substantially denature. The term "substantially" means at least 60%, and preferably at least 90% or more preferably at least 98% in a given denatured or undenatured form. The melting temperature for the duplex of the reference blocking sequence and the target strands will always be less than the melting temperature of the duplex of the reference blocking sequence and the complementary reference strand because the former contains a mismatch whereas the latter does not.

After preferential denaturation, the temperature of the reaction mixture is reduced so as to permit the primer pairs to anneal to the free target and reference strands in the reaction mixture. Again, assuming that single stranded reference blocking oligonucleotides are added in excess at the beginning of the process, at this point in the cycle there are, theoretically, two free strands of the target sequence compared to the initial denaturation step and only one free reference strand. The other reference strand is hybridized with the reference blocking sequence, and is therefore unavailable for amplification. The annealed primers are then extended, thus resulting in exponential amplification of the target sequence, while the reference strand is only amplified linearly. Accordingly, the target sequence is gradually enriched relative to the reference sequence in the sample during the COLD-PCR cycles.

The method is likely repeated ten to thirty cycles or more. It has been found to substantially increase enrichment of target amplicons and decrease cycle time for full COLD-PCR. It is also able to enrich homozygous mutations, which would not form heteroduplexes in the prior full COLD-PCR protocol.

The length of the reference blocking sequence can be equal to, or smaller or larger than the length of the target or reference sequences. In a preferred embodiment, the reference blocking sequence is several bases smaller than the target and reference sequences, on each side of the sequence so that the primers do not bind appreciably to the reference sequence. Hence, the reference blocking sequence cannot be extended by the primers that amplify the target sequence. To this end, optionally the 3' OH end of the reference blocking sequence can be blocked to DNA-polymerase extension. Also, optionally, the 5'-end of the reference blocking sequence may be designed with nucleotide sequence that partially overlaps the primer binding sites such that 5' to 3' exonucleolysis by Taq DNA polymerases (i.e. degradation of the hybridized reference blocking sequence) may be prevented.

As mentioned, the reference sequence is single stranded or double stranded. In a preferred embodiment, the reference blocking sequence is single stranded nucleic acid. However, the reference blocking sequence can take other forms, such as a chimera between single stranded DNA, RNA, peptide nucleic acid (PNA) or locked nucleic acid (LNA), or another modified nucleotide. The PNA or LNA positions on the chimera sequence can be selected to match positions where mutations are likely, so as to maximize the effect of potential mismatches at those positions. The reference blocking sequence can be also single stranded PNA or single stranded DNA.

Other embodiments and advantages of the invention may be apparent to those skilled in the art upon reviewing the drawings and the following detailed description.

BRIEF DESCRIPTION OF THE DRAWINGS

FIG. 1A is an illustration of the enrichment protocol and an exemplary 167 bp p53 exon 8 sequence. The formation of mismatches anywhere along the sequence during PCR enables preferential denaturation and amplification of minor (mutant) alleles at every PCR cycle. FIG. 1B shows a replacement of PCR with the enrichment method, namely all PCR-based genetic testing assays stand to benefit by mutation-enrichment during the PCR step that precedes them.

FIG. 3 is a schematic drawing illustrating a 60 bp reference blocking sequence for implementing one embodiment of the invention. An 87 bp amplicon is preliminarily amplified using the underlined primers. A complementary reference blocking sequence is designed for each strand and contains a 3' non-extensible phosphate group.

DETAILED DESCRIPTION

Definitions

Figure 1:
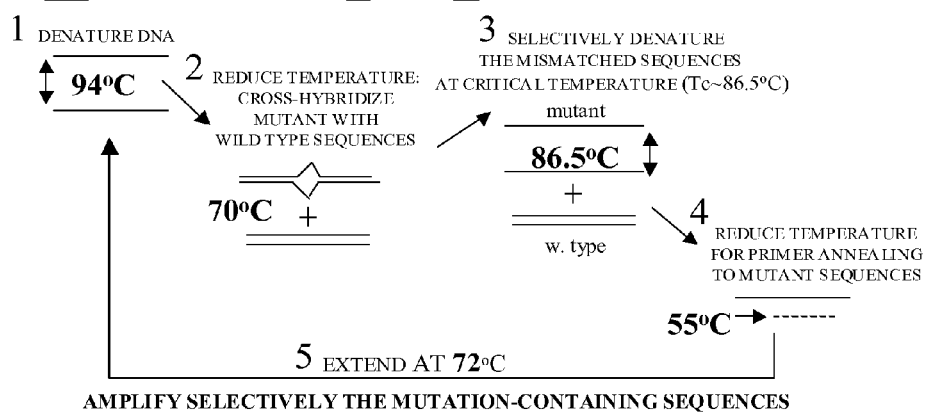
FIG. 1 illustrates a prior art embodiment of full COLD-PCR for selectively enriching a target sequence as described in the prior patent application entitled "Enrichment of a Target Sequence", International Application No. PCT/US2008/009248, now U.S. Ser. No. 12/671,295, and incorporated herein by reference.
Figure 1:
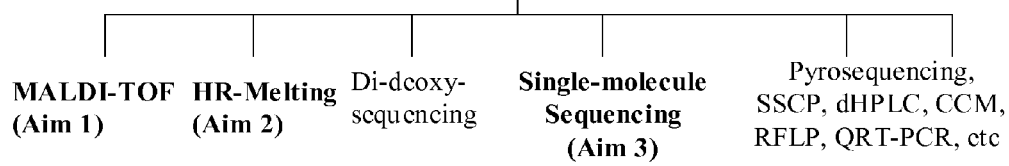

As used herein, the term "enriching a target sequence" refers to increasing the amount of a target sequence and increasing the ratio of target sequence relative to the corresponding reference sequence in a sample. For example, where the ratio of target sequence to reference sequence is initially 5% to 95% in a sample, the target sequence may be preferentially amplified in an amplification reaction so as to produce a ratio of 70% target sequence to 30% reference sequence. Thus, there is a 14-fold enrichment of the target sequence relative to the reference sequence.

As used herein the term "target sequence" refers to a nucleic acid that is less prevalent in a nucleic acid sample than a corresponding reference sequence. The target sequence makes-up less than 50% of the total amount of reference sequence+target sequence in a sample. The target sequence may be a mutant allele. For example, a sample (e.g., blood sample) may contain numerous normal cells and few cancerous cells. The normal cells contain non-mutant or wild-type alleles, while the small number of cancerous cells contains somatic mutations. In this case the mutant is the target sequence while the wild-type sequence is the reference sequence.

As used herein, a "target strand" refers to a single nucleic acid strand of a target sequence.

The target sequence must be at least 50% homologous to the corresponding reference sequence, but must differ by at least one nucleotide from the reference sequence. Target sequences are amplifiable via PCR with the same pair of primers as those used for the reference sequence.

As used herein, the term "reference sequence" refers to a nucleic acid that is more prevalent in a nucleic acid sample than a corresponding target sequence. The reference sequence makes-up over 50% of the total reference sequence+target sequence in a sample. Preferably the reference sequence is expressed at the RNA and/or DNA level 10×, 15×, 20×, 25×, 30×, 35×, 40×, 45×, 50×, 60×, 70×, 80×, 90× 100×, 150×, 200× or more than the target sequence. As used herein, a "reference strand" refers to a single nucleic acid strand of a reference sequence.

As used herein, the term "wild-type" refers to the most common polynucleotide sequence or allele for a certain gene in a population. Generally, the wild-type allele will be obtained from normal cells.

As used herein, the term "mutant" refers to a nucleotide change (i.e., a single or multiple nucleotide substitution, deletion, or insertion) in a nucleic acid sequence. A nucleic acid which bears a mutation has a nucleic acid sequence (mutant allele) that is different in sequence from that of the corresponding wild-type polynucleotide sequence. The invention is broadly concerned with somatic mutations and polymorphisms. The methods of the invention are especially useful in selectively enriching a mutant allele which contains between about 1 and 10 nucleotide sequence changes, although is useful even with a higher number of sequence changes. A mutant allele will typically be obtained from diseased tissues or cells and is associated with a disease state.

As used herein the term "melting temperature" or "$T_m$" refers to the temperature at which a polynucleotide dissociates from its complementary sequence. Generally, the $T_m$ may be defined as the temperature at which one-half of the Watson-Crick base pairs in a double stranded nucleic acid molecule are broken or dissociated (i.e., are "melted") while the other half of the Watson-Crick base pairs remain intact in a double stranded conformation. In other words the $T_m$ is defined as the temperature at which 50% of the nucleotides of two complementary sequences are annealed (double strands) and 50% of the nucleotides are denatured (single strands). $T_m$ therefore defines a midpoint in the transition from double-stranded to single-stranded nucleic acid molecules (or, conversely, in the transition from single-stranded to double-stranded nucleic acid molecules).

The $T_m$ can be estimated by a number of methods, for example by a nearest-neighbor calculation as per Wetmur 1991 (Wetmur, J. G. 1991. DNA probes: applications of the principles of nucleic acid hybridization. Crit Rev Biochem Mol Biol 26: 227-259,) and by commercial programs including Oligo™ Primer Design and programs available on the internet. Alternatively, the $T_m$ can be determined though actual experimentation. For example, double-stranded DNA binding or intercalating dyes, such as Ethidium bromide or SYBR-green (Molecular Probes) can be used in a melting curve assay to determine the actual $T_m$ of the nucleic acid. Additional methods for determining the $T_m$ of a nucleic acid are well known in the art. Some of these methods are listed in the inventor's prior patent application entitled "Enrichment of a Target Sequence", International Application No. PCT/US2008/009248, now U.S. Ser. No. 12/671,295, incorporated by reference herein.

As used herein, "reference blocking sequence" is an engineered single stranded or double stranded nucleic acid sequence, such as an oligonucleotide and preferably has a length smaller than the target sequence. In a preferred embodiment, the reference blocking sequence is several bases smaller than the reference sequence, on each side of the sequence so that the primers do not bind appreciably to the reference sequence. Optionally, the 3' OH end of the reference blocking sequence is blocked to DNA-polymerase extension, the 5-end is modified to prevent 5' to '3 exonucleolysis by Taq DNA polymerases. The reference blocking sequence can also take other forms which remain annealed to the reference sequence when the reaction mixture is subject to the critical temperature "$T_c$", such as a chimera between single stranded DNA, RNA, peptide nucleic acid (PNA) or locked nucleic acid (LNA), or another modified nucleotide.

As used in connection with the present invention, the term "critical temperature" or "$T_c$" refers to a temperature selected to preferentially denature duplexes of target strands and the reference blocking sequence. The critical temperature ($T_c$) is selected so that duplexes consisting of the reference blocking strands and complementary reference strands remain substantially undenatured when the reaction mixture is incubated at $T_c$ yet duplexes consisting of the reference blocking strands and the target strands substantially denature. The term "substantially" means at least 60%, and preferably at least 90% or more preferably at least 98% in a given denatured or undenatured form. In the examples provided below, the selected critical temperature "$T_c$" for the intermediate incubation step is 84.5° C., whereas the first denaturing temperature is 95° C.

As used herein, "primer pair" refers to two primers that anneal to opposite strands of a target and reference sequence so as to form an amplification product during a PCR reaction. The target and the reference sequence should be at least 25 bases in order to facilitate primer attachment. The primer pair is designed so as to have a $T_m$ lower than the $T_c$ of the reaction.

As used herein, "homology" refers to the subunit sequence similarity between two polymeric molecules, e.g., two polynucleotides or two polypeptides. An example of an algorithm that is suitable for determining percent sequence identity and sequence similarity are the BLAST and BLAST 2.0 algorithms, which are described in Altschul et al., Nucleic Acids Res. 25:3389-3402 (1997) and Altschul et al., J. Mol, Biol. 215:403-410 (1990), respectively, Software for performing BLAST analyses is publicly available through the National Center for Biotechnology Information.

Nucleic Acid Amplification Generally

In one embodiment, a nucleic acid sample utilized in the method of the invention comprises genomic DNA having a target and reference sequence. In another embodiment, the nucleic acid sample of the method of the invention comprises target and reference sequences that were previously amplified in a nucleic acid amplification reaction. The skilled artisan will appreciate that there are many methods available to amplify a nucleic acid. Perhaps the most popular method is the polymerase chain reaction (PCR; for example, see, U.S. Pat. Nos. 4,683,195 and 4,683,202, as well as Saiki et al., Science 230:1350-1354 (1985) and Gyllensten et al., PNAS (USA) 85:7652-7656 (1985)). A preferred variation of the PCR method is asymmetrical PCR (for example, see Mao et al., Biotechniques 27(4):674-678 (1999); Lehbein et al., Electrophoresis 19(8-9):1381-1384 (1998); Lazaro et al., Mol. Cell. Probes 6(5):357-359 (1992); and U.S. Pat. No. 6,197,499). Other amplification methods include, but are not limited to, strand displacement amplification (SDA) (see, Walker et al., Nucleic Acids Res. 20(7):1691-1696 (1992), as well as U.S. Pat. Nos. 5,744,311, 5,648,211 and 5,631,147), rolling circle amplification (RCA) (see PCT publication WO 97/19193), nucleic acid sequence-based amplification (NASBA) (see Compton, Nature 350:91-92 (1991); as well as U.S. Pat. Nos. 5,409,818 and 5,554,527), transcript mediated amplification (TMA) (see Kwoh et al., PNAS (USA) 86:1173-1177 (1989), as well as U.S. Pat. No. 5,399,491), self sustained sequence replication (3SR) (see Guatelli et al., PNAS (USA) 87:1874-1879 (1990) and ligase chain reaction (LCA) (see U.S. Pat. Nos. 5,427,930 and 5,792,607).

In its simplest form, PCR is an in vitro method for the enzymatic synthesis of specific DNA sequences, using two oligonucleotide primers that hybridize to opposite strands and flank the region of interest in the target DNA. A repetitive series of reaction steps involving template denaturation, primer annealing and the extension of the annealed primers by DNA polymerase results in the exponential accumulation of a specific fragment whose termini are defined by the 5' ends of the primers. PCR is reported to be capable of producing a selective enrichment of a specific DNA sequence by a factor of 109 relative to other sequences in genomic DNA. The PCR method is also described in Saiki et al., 1985, *Science* 230: 1350.

PCR is performed using template DNA (target and reference sequences) (at least 1 fg; more usefully, 1-1000 ng) and at least 25 pmol of oligonucleotide primers. A typical reaction mixture includes: 2 μl of DNA, 25 pmol of oligonucleotide primer, 2.5 μl of a suitable buffer, 0.4 μl of 1.25 μM dNTP, 2.5 units of Taq DNA polymerase (Stratagene) and deionized water to a total volume of 25 μl. PCR is performed using a programmable thermal cycler.

The length and temperature of each step of a PCR cycle, as well as the number of cycles, are adjusted according to the stringency requirements in effect. Annealing temperature and timing are determined both by the efficiency with which a primer is expected to anneal to a template and the degree of mismatch that is to be tolerated. The ability to optimize the stringency of primer annealing conditions is well within the knowledge of one of moderate skill in the art. An annealing temperature of between 30° C. and 72° C. is used. Initial denaturation of the template molecules normally occurs at between 92° C. and 99° C. for 4 minutes, followed by 20-40 cycles consisting of denaturation (94-99° C. for 15 seconds to 1 minute), annealing (temperature determined as discussed above; 1-2 minutes), and extension (72° C. for 1 minute). The final extension step is generally carried out for 4 minutes at 72° C., and may be followed by an indefinite (0-24 hour) step at 4° C.

PCR utilizes a nucleic acid polymerase, or enzyme that catalyzes the polymerization of nucleoside triphosphates. Generally, the enzyme will initiate synthesis at the 3'-end of the primer annealed to the target sequence, and will proceed in the 5'-direction along the template. Known DNA polymerases include, for example, *E. coli* DNA polymerase I, T7 DNA polymerase, *Thermus thermophilus* (Tth) DNA polymerase, *Bacillus stearothermophilus* DNA polymerase, *Thermococcus litoralis* DNA polymerase, *Thermus aquaticus* (Taq) DNA polymerase and *Pyrococcus furiosus* (Pfu) DNA polymerase. The term "nucleic acid polymerase" also encompasses RNA polymerases. If the nucleic acid template is RNA, then "nucleic acid polymerase" refers to an RNA-dependent polymerization activity, such as a reverse transcriptase.

The enrichment procedures of the present invention are performed in a PCR device such as a thermocycler, or more preferably under real-time reaction conditions in a real-time PCR device. Real-time reaction conditions further utilize a nucleic acid detection agent (e.g., dye or probe) in order to measure/detect the PCR product as it is produced.

Samples

As used herein, "sample" refers to any substance containing or presumed to contain a nucleic acid of interest (target and reference sequences) or which is itself a nucleic acid containing or presumed to contain a target nucleic acid of interest. The term "sample" thus includes a sample of nucleic acid (genomic DNA, cDNA, RNA), cell, organism, tissue, fluid, or substance including but not limited to, for example, plasma, serum, spinal fluid, lymph fluid, synovial fluid, urine, tears, stool, external secretions of the skin, respiratory, intestinal and genitourinary tracts, saliva, blood cells, tumors, organs, tissue, samples of in vitro cell culture constituents, natural isolates (such as drinking water, seawater, solid materials), microbial specimens, and objects or specimens that have been "marked" with nucleic acid tracer molecules.

Nucleic acid sequences of the invention can be amplified from genomic DNA. Genomic DNA can be isolated from tissues or cells according to the following method. Alternatively nucleic acids sequences of the invention can be isolated from blood by methods well known in the art.

To facilitate detection of a variant form of a gene from a particular tissue, the tissue is isolated. To isolate genomic DNA from mammalian tissue, the tissue is minced and frozen in liquid nitrogen. Frozen tissue is ground into a fine powder with a prechilled mortar and pestle, and suspended in digestion buffer (100 mM NaCl, 10 mM Tris-HCl, pH 8.0, 25 mM EDTA, pH 8.0, 0.5% (w/v) SDS, 0.1 mg/ml proteinase K) at 1.2 ml digestion buffer per 100 mg of tissue. To isolate genomic DNA from mammalian tissue culture cells, cells are pelleted by centrifugation for 5 min at 500×g, resuspended in 1-10 ml ice-cold PBS, repelleted for 5 min at 500×g and resuspended in 1 volume of digestion buffer.

Samples in digestion buffer are incubated (with shaking) for 12-18 hours at 50° C., and then extracted with an equal volume of phenol/chloroform/isoamyl alcohol. If the phases are not resolved following a centrifugation step (10 min at 1700×g), another volume of digestion buffer (without proteinase K) is added and the centrifugation step is repeated. If a thick white material is evident at the interface of the two phases, the organic extraction step is repeated. Following extraction the upper, aqueous layer is transferred to a new tube to which will be added ½ volume of 7.5 M ammonium acetate and 2 volumes of 100% ethanol. The nucleic acid is pelleted by centrifugation for 2 min at 1700×g, washed with 70% ethanol, air dried and resuspended in TE buffer (10 mM Tris-HCl, pH 8.0, 1 mM EDTA, pH 8.0) at 1 mg/ml. Residual RNA is removed by incubating the sample for 1 hour at 37° C. in the presence of 0.1% SDS and 1 μg/ml DNase-free RNase, and repeating the extraction and ethanol precipitation steps. The yield of genomic DNA, according to this method is expected to be approximately 2 mg DNA/1 g cells or tissue (Ausubel et al., supra). Genomic DNA isolated according to this method can be used according to the invention.

The target DNA may also be extracted from whole blood. For example, blood may be drawn by standard methods into a collection tube, preferably comprising siliconized glass, either without anticoagulant for preparation of serum, or with EDTA, sodium citrate, heparin, or similar anticoagulants, most preferably EDTA, for preparation of plasma. The preferred method, although not absolutely required, is that plasma or serum be fractionated from whole blood. Plasma or serum may be fractionated from whole blood by centrifugation, preferably gentle centrifugation at 300 to 800×g for 5-10 minutes, or fractionated by other standard methods. Since heparin may interfere with PCR, use of heparinized blood may require pretreatment with heparinase. Thus, EDTA is the preferred anticoagulant for blood specimens. Either freshly-collected blood plasma or serum, or frozen (stored) and subsequently thawed plasma or serum can be used in the methods of the invention. Stored plasma or serum should be kept at −20° C. to −70° C., and freshly-collected plasma or serum kept refrigerated or maintained on ice until use. The DNA may then be extracted by methods well known in the art.

The method of the present invention can be used to detect whether methylation has occurred in a target sequence. The methylation detection method comprises a chemical or enzymatic approach for methylation-sensitive treatment of DNA. Chemical treatments include the incubation of DNA with sodium bisulfite, which selectively converts non-methylated cytosines to uracils. The DNA is first heat-denatured and then treated with 5M bisulfite, pH 5-7. Pretreatment of genomic DNA to remove pre-existing uracils is used prior to bisulfite treatment. This pretreatment consists of uracil glycosylase treatment in the presence of 5 mM hydroxylamine, pH 7.

Because the methylated cytosines of the target sequence are converted to uracils, they will now form mismatches when duplexed with the reference blocking sequence in the hybridization cool down step of full COLD-PCR (in the presence of reference blocking sequence).

Full COLD-PCR in the Absence of Reference Blocking Sequence (Prior Art)

FIG. 1 illustrates the prior art procedure known as full COLD-PCR for enriching a target sequence in a nucleic acid sample containing a target and reference sequence, as explained the above incorporated U.S. application Ser. No. 12/671,295, entitled "Enrichment of a target Sequence". FIG. 1 is a reproduction of FIG. 1 in the above incorporated patent application.

The target and reference sequences can be obtained from a variety of sources including, genomic DNA, cDNA, viral DNA, mammalian DNA, fetal DNA or bacterial DNA. While the reference sequence is generally the wild-type allele and the target sequence is the mutant allele, the reverse may also be true. The mutant allele may include any one or more nucleotide deletions, insertions or alterations. In some embodiments, the mutant allele is a somatic mutation. In other embodiments, the target sequence is methylated DNA while the reference sequence is un-methylated DNA.

The method includes subjecting the amplification reaction mixture to a first denaturing temperature (FIG. 1A, Step 1) that is above the melting temperature "$T_m$" of a reference sequence. The $T_m$ of a nucleic acid can be determined through experimentation or estimated by calculation. The skilled artisan is well aware of numerous well known methods for determining the $T_m$ of a nucleic acid some of which are described herein. The first denaturing temperature is generally selected as one would generally select the denaturing temperature of a PCR reaction and should be sufficiently high so as to allow the full denaturing of the target and reference sequences (e.g., 94° C.). In one embodiment, the first denaturing temperature is about 1° C. to 30° C. above the $T_m$ of the reference sequence, more preferably the $T_m$ of the reference sequence is about 5° C. to 20° C. above the $T_m$ of the reference sequence.

Next, the temperature of the amplification reaction mixture is decreased allowing the target sequences and reference sequences to hybridize (FIG. 1A, Step 2). This annealing step results in the formation of duplexes of target-target, reference-reference and target-reference sequences, but should be optimized to form target-reference duplexes. The PCR primers used in the method are designed to have a melting temperature that prevents them from binding to the target and reference sequences at this intermediate temperature. As mentioned above, the requirement of target-reference hybridization and the relatively large amount of time needed for cool down (FIG. 1A, Step 2) has been found to limit the effectiveness of full COLD-PCR at least in some applications.

The target-reference hybridization duplexes are then preferentially denatured by increasing the temperature of the reaction mixture to the $T_c$ (FIG. 1A, Step 3). The $T_c$ or critical temperature in FIG. 1 is selected to be below the $T_m$ of the reference sequence yet above the $T_m$ of the target-reference duplex. As mentioned previously, when the target sequence and reference sequence cross hybridize, minor sequence differences of one or more single nucleotide mismatch anywhere along a double stranded DNA sequence will generate a small but predictable change in the melting temperature ($T_m$) for that sequence (Lipsky, R. H., et al. (2001) *Clin Chem*, 47, 635-644; Liew, M., et al. (2004) *Clin Chem*, 50, 1156-1164). Depending on the exact sequence context and position of the mismatch, melting temperature changes in the range of 0.1-20° C. are possible. The $T_c$ is generally applied (FIG. 1A, Step 3) from about 1 second to 5 minutes, more preferably 5 seconds to 30 seconds. It is possible to oscillate between steps 3 and 2 for multiple cycles if desired.

After the preferential denaturing of the target-reference hybridization duplexes, the temperature of the reaction mixture is reduced so as to allow one or more primers to anneal to the target sequence (FIG. 1A, Step 4). The annealed primers are then extended by a nucleic acid polymerase (FIG. 1A, Step 5), thus enriching the target sequence in the population of nucleic acids contained in the sample.

The steps of the method are generally repeated for multiple cycles in order to get sufficient amplification of the target and reference sequences. In one embodiment, the steps of the method are repeated for 5-40 cycles and more preferably 10-30 cycles. The optimal number of cycles can be determined by one of ordinary skill in the art. Preferably, the present methods are performed in a PCR device, more preferably under real-time reaction conditions in a real-time detection PCR device, such as the SMARTCYCLER real-time PCR device (Cepheid, Sunnyvale, Calif.) and the Mx3005P real-time PCR device (Stratagene, La Jolla, Calif.). In this embodiment, the reaction mixture may include a nucleic acid detection agent (e.g., nucleic acid detection dye such as SYBR Green dye or LC-Green dye or a probe operatively coupled to a fluorescent dye) for quantifying and/or monitoring the amplification products of the reaction. Once the enrichment of the target sequence is complete the sample may be further processed, e.g., subjected to a sequencing reaction. The enriched alleles may be further processed by a variety of procedures including: MALDI-TOF, HR-Melting, Di-deoxy-sequencing, Single-molecule sequencing, second generation high throughput sequencing, pyrosequencing, RFLP, digital PCR and quantitative-PCR (See FIG. 1B). A more detail description of these processing technologies as well as diagnostic assays is included in the above mentioned U.S. application Ser. No. 12/671,295, entitled "Enrichment of a target Sequence", and incorporated herein by reference.

Full COLD-PCR Cycle with Excess Reference Blocking Sequence in Reaction Mixture

Figure 2:
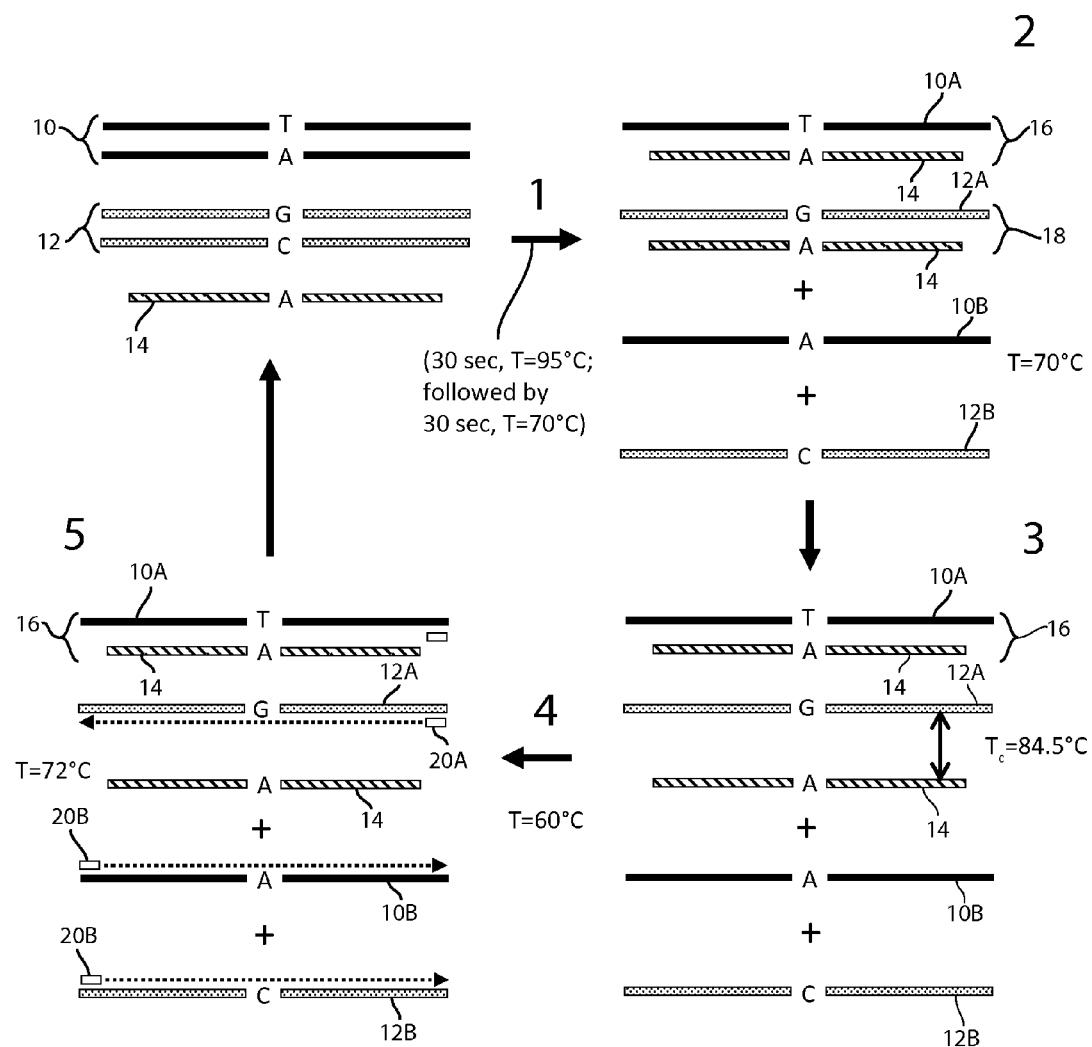
FIG. 2 illustrates the principle of the present invention which improves full COLD-PCR via the presence of an excess amount of a reference blocking sequence in the amplification reaction mixture.

FIG. 2 illustrates enrichment of a target sequence in accordance with the modified full COLD-PCR method of the present invention. To begin (FIG. 2, step 1), the nucleic acid sample contains a double-stranded reference sequence 10 (e.g., a wild-type sequence) and contains a double-stranded target sequence 12 (e.g., a mutant sequence). The amplification reaction mixture contains the sample, other PCR ingredients, and in accordance with the invention a reference blocking sequence 14 at an excess concentration level, such as 25 nM. In FIG. 2, the depicted reference blocking sequence 14 is a single-stranded nucleic acid sequence complementary with one of the strands 10A of the reference sequence 10 between its primer sites.

The reaction mixture in step 1 of FIG. 2 is subjected to a first denaturing temperature, e.g. 95° C. for 30 seconds, which results in denatured strands of the reference sequence 10A, 10B and the target sequence 12A, 12B. The reaction mixture is then cooled to promote hybridization, e.g., 70° C. for 30 seconds, which is a dramatic reduction from the normal 8 minute cool down in the prior art. Since the cool down occurs in the presence of an excess amount of reference blocking sequences 14, the reference blocking sequences 14 preferentially hybridize with the complementary strand 10A of the reference sequence and also the complementary strand 12A of the target sequence. Step 2 in FIG. 2 illustrates the state of the reaction mixture after the hybridization cool down to 70° C. In addition to heteroduplexes 16 of the reference blocking sequence 14 and the complementary reference strand 10A and heteroduplexes 18 of the reference blocking sequence 14 and the complementary target strand 12A, the reaction mixture also contains the denatured negative strands 10B and 12B of the reference and target sequences, respectively.

In step 3 of FIG. 2, the reaction mixture is then subjected to the critical temperature "$T_c$", e.g., 84.5° C., which is chosen to permit preferential denaturation of the heteroduplexes 18 of the target strand 12A and reference blocking sequence 14. The critical temperature ($T_c$) is selected so that duplexes 16 of the reference blocking strands 14 and the complementary reference strands 10A remain substantially undenatured when the reaction mixture is incubated at "$T_c$". The melting temperature for the duplex 18 of the reference blocking sequence 14 and the target strand 10B will always be less than the melting temperature of the duplex 16 of the reference blocking sequence 14 and the complementary reference strand 10A because the reference blocking sequence 14 is fully complementary with at least a portion of the reference strand 10A, and there will be at least one mismatch with the target strand 12A.

Referring to step 4 of FIG. 2, after preferential denaturation, the temperature of the reaction mixture is reduced, e.g., 60° C., to permit the primer pair 20A, 20B to anneal to the free target strands 12A, 12B and the free reference strand 10B in the reaction mixture. Reference number 20A refers to the forward primer and reference number 20B refers to the reverse primer. As described previously, the target sequence 12 is amplifiable via the same pair of primers 20A, 20B as those used for the reference sequence 10. Step 5 of FIG. 2 illustrates two free strands 12A, 12B of the target sequence compared to the initial denaturation step and only one free reference strand 10B. The other reference strand 10A is hybridized with the reference blocking sequence 14, and is therefore unavailable for amplification. The temperature of the reaction mixture is then raised, e.g. 72° C., to extend the annealed primers 20A, 20B, thus enriching the concentration of the target sequence 12 in the reaction mixture relative to the reference sequence 10. The method is likely repeated five to thirty cycles.

The method illustrated in FIG. 2 can and should be optimized for individual protocols. Such protocols can be embodied in software, if desired, for operating various PCR and real-time PCR equipment.

Design Considerations for the Preferred Reference Blocking Sequence

As mentioned, the reference blocking sequence can take many forms, yet the preferred form is single stranded, non-extensible DNA. More specifically, the preferred reference blocking sequence has the following characteristics:

(a) comprises single-stranded DNA of up to 200 bp in length;
(b) has a length that is several bases smaller than the target sequence (e.g. 8-12 bases on each side of the sequence) so that the primers do not bind appreciably to the reference sequence when annealed to the reference blocking sequence; and also do not bind appreciably to the reference blocking sequence itself; and
(c) contains a 3'-end that is blocked to DNA-polymerase extension.

Such a reference blocking sequence can be synthesized in one of the several methods. First, the reference blocking sequence can be made by direct synthesis using standard oligonucleotide synthesis methods that allow modification of the 3'-end of the sequence. The 3'-end may contain a phosphate group, an amino-group, a di-deoxy-nucleotide or any other moiety that blocks 5' to 3' polymerase extension. Alternatively, the reference blocking sequence can be made by polymerase synthesis during a PCR reaction that generates single stranded DNA as the end product. In this case, the generated single stranded DNA corresponds to the exact sequence necessary for the reference blocking sequence.

Methods to synthesize single stranded DNA via polymerase synthesis are several and well known to those skilled in the art. For example, asymmetric PCR or LATE PCR would be suitable. Alternatively, a single stranded DNA reference blocking sequence can be synthesized by binding double stranded PCR product on solid support. This is accomplished by performing a standard PCR reaction, using a primer pair one of which is biotinylated. Following PCR, the PCR product is incubated with a streptavidin-coated solid support (e.g. magnetic beads) and allowed to bind to the beads. Subsequently, the temperature is raised to 95° C. for 2-3 minutes to denature DNA and release to the solution the non-biotinylated DNA strand from the immobilized PCR product. The magnetic beads with the complementary DNA strand are then removed and the single stranded product remaining in the solution serves as the reference blocking sequence.

Before the single stranded reference blocking sequence is used, the 3'-end is preferably blocked to polymerase extension. This can be accomplished in several ways well known to those skilled in the art. For example, a reaction with Terminal Deoxynucleotide Transferase (TdT) can be employed, in the presence of di-deoxy-nucleotides (ddNTP) in the solution, to add a single ddNTP to the end of the single stranded reference blocking sequence. ddNTPs serve to block polymerase extension. Alternatively, an oligonucleotide template complementary to the 3'-end of the reference blocking sequence can be used to provide a transient double stranded structure. Then, polymerase can be used to insert a single ddNTP at the 3'-end of the reference blocking sequence opposite the hybridized oligonucleotide.

In another method to synthesize the reference blocking sequence in a double stranded form, a conventional PCR is carried out to amplify a wild type version of the sequence of interest, using primers that contain rare enzymatic restriction sites. Following PCR amplification, restriction enzymes are applied to digest both ends of the PCR product and create overhangs. These overhangs are then subjected to polymerase extension in the presence of di-deoxy-nucleotides, thereby blocking the 3'-end on both sides from further extension. The double-stranded, 3'-end blocked PCR product can then serve as a double stranded reference blocking sequence.

Specific Examples of Oligonucleotide-Synthesis-Generated Reference Blocking Sequences Two reference blocking sequences were synthesized: a 60 bp (RBS60) and a 90 bp (RBS90) reference blocking sequence corresponding to sections of p53 exon 8. Table 1 contains the listed sequences for the synthesized RBS60 and RBS90 reference blocking sequences. Both the RBS60 and the RBS90 sequence were synthesized with a 3'-blocking phosphate group by Integrated DNA Technologies, Inc. Cell lines with mutations in the same exon 8 fragment were used to test the method (see, listing in Table 1).

FIG. 3 is a schematic drawing illustrating the use of the RBS60 reference blocking sequence in connection with modified, full COLD-PCR enrichment. An 87 bp amplicon is preliminarily amplified using the underlined primers. The complementary reference blocking sequence (RBS60) is designed for the reference strand in FIG. 3. As apparent from FIG. 3 RBS60 prevents the primers from binding, and contains a 3' phosphate group to prevent extension.

Protocol for RBS60: A 167 bp sequence from p53 exon 8 was initially amplified using conventional PCR and the primers Ex8-167F and Ex8-167R (Table 1). The genomic DNA used was either wild-type DNA, or a mixture of 3% mutant DNA into wild-type DNA. The mutant cell lines used, that contain specific mutations, are listed in Table 1.

The PCR product was then diluted 500-fold. Then, the modified full-COLD-PCR reaction in the presence of 25 nM reference blocking sequence RBS60, and 200 nM primers 87f and 87r that amplify a region nested within the 167 bp fragment was implemented. Phusion™ polymerase (New England Biolabs) was used for the amplification. The full-COLD-PCR program was: 5 cycles of conventional PCR (30 sec at 95° C.; 30 sec 60° C.; 1 min 72° C.); then 25 cycles of full COLD-PCR (30 sec at 95° C.; 30 sec at 70° C.; then 3 sec at $T_c$=84.5° C., then 30 sec at 60° C.; 1 min at 72° C.)×25. Alternatively, full COLD-PCR (in the absence of RBS60) was performed by applying the exact same program as for full COLD-PCR in the presence of RBS60, but by omitting the RBS60 from the reaction mixture. Following full COLD-PCR in the presence of RBS60 (and full COLD-PCR (no RBS60), and fast COLD-PCR, and regular PCR) the products were sequenced by using the longer primer 30T-p53-87F.

Protocol for RBSS90: The same procedure was applied for RBS90 as detailed for RBS60; but with the difference that the primers set for the nested full COLD-PCR were p53-ex8-115F and p53-ex8-115R and the $T_c$ applied for RBS90 was $T_c$=84.4° C.

TABLE 1

| Oligo | Sequence (5' to 3') | Source |
|---|---|---|
| Reference Blocking Sequence 1 (RBS60) | | |
| Ex8-167F | GCTTCTCTTTTCCTATCCTG (SEQ ID NO: 1) | Li et al (2008) |
| Ex8-167R | CTTACCTCGCTTAGTGCT (SEQ ID NO: 2) | Li et al (2008) |
| 87f | TGGTAATCTACTGGGACG (SEQ ID NO: 3) | Li et al (2008) |
| 87r | CGGAGATTCTCTTCCTCT (SEQ ID NO: 4) | Li et al (2008) |
| 30T-p53-87F | TTTTTTTTTTTTTTTTTTTT TTTTTTTTTTGGTAATCTACT GGGACG (SEQ ID NO: 5) | |
| 60refseq-for | GGACGGAACAGCTTT (SEQ ID NO: 6) | |
| 60refseq-rev | CTGGCCGCGTGTCTC (SEQ ID NO: 7) | |
| RBS60 | 5'CTCTGTGCGCCGGTCTCTC CCAGGACAGGCACAAACACGC ACCTCAAAGCTGTTCCGTCC-phos-3' (SEQ ID NO: 8) | |
| Reference Blocking Sequence 2 (RBS90) | | |
| Ex8-167F | GCTTCTCTTTTCCTATCCTG (SEQ ID NO: 9) | Li et al (2008) |
| Ex8-167R | CTTACCTCGCTTAGTGCT (SEQ ID NO: 10) | Li et al (2008) |

TABLE 1-continued

| Oligo | Sequence (5' to 3') | Source |
|---|---|---|
| p53-ex8-115F | TTGCTTCTCTTTTCCTAT (SEQ ID NO: 11) | |
| p53-ex8-115R | TTTTTTTTTTTTTTTTTTTT TTTTTTTTTTTTTTTTTTTT GCTTCTCTTTTCCTATCC (SEQ ID NO: 12) | |
| RBS90 | 5'CTTCCTCTGTGCGCCGGTCT CTCCCAGGACAGGCACAAACAC GCACCTCAAAGCTGTTCCGTCC CAGTAGATTACCACTACTCAGG ATAG-phos-3' (SEQ ID NO: 13) | |

Results: Representative results are depicted in FIGS. 4 through 7 for the RBS60 and FIG. 8 for RBS90. In FIGS. 4 through 7, modified, full COLD-PCR (in presence of RBS60) is compared with full COLD-PCR (no RBS60), Fast COLD-PCR, and conventional PCR.

Figure 4:
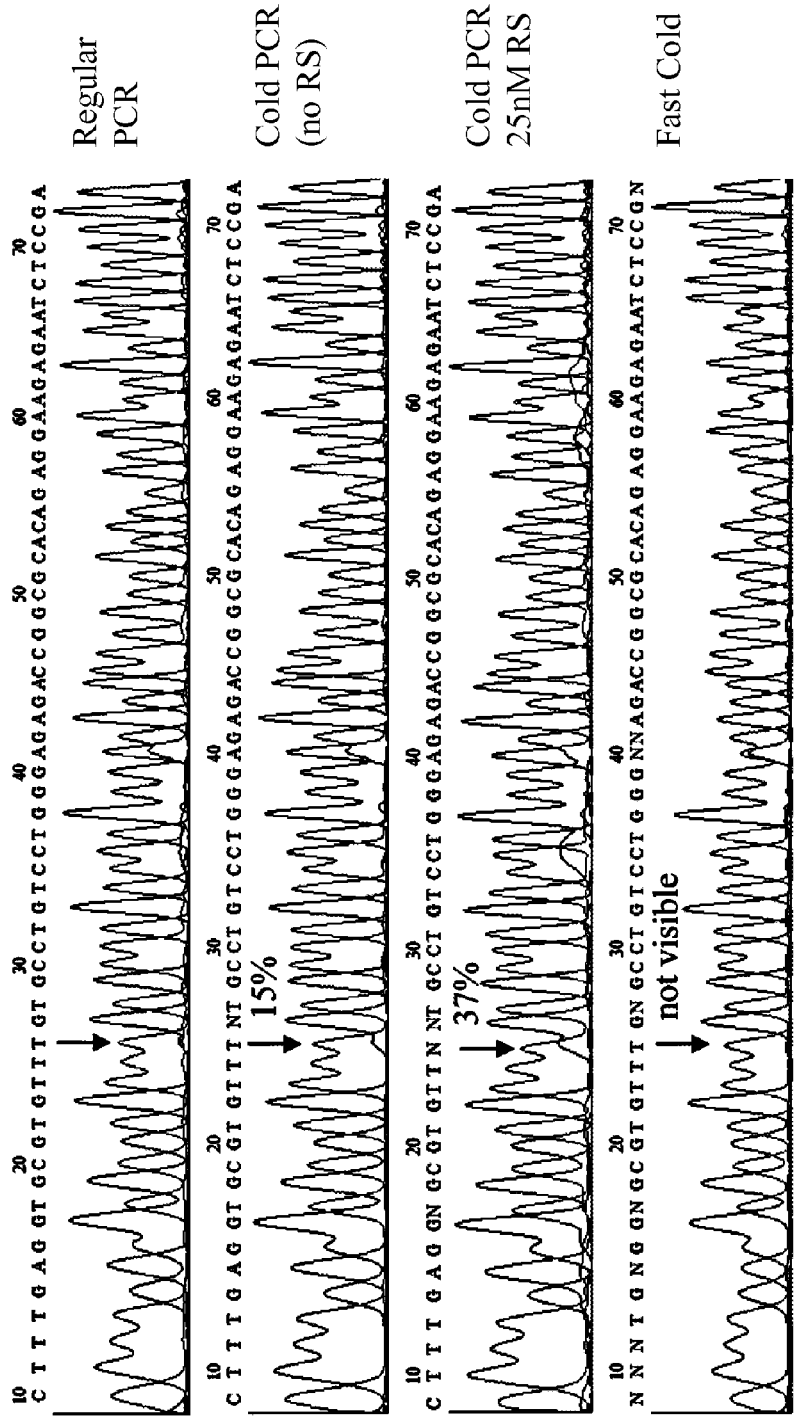
FIG. 4 displays Sanger sequencing data for the enrichment of PFSK-1 mutant alleles from samples processed using regular PCR, full COLD-PCR without the use of a reference blocking sequence in the reaction mixture; full COLD-PCR with an excess of reference blocking sequence in the reaction mixture, and fast COLD-PCR, respectively.
Figure 5:
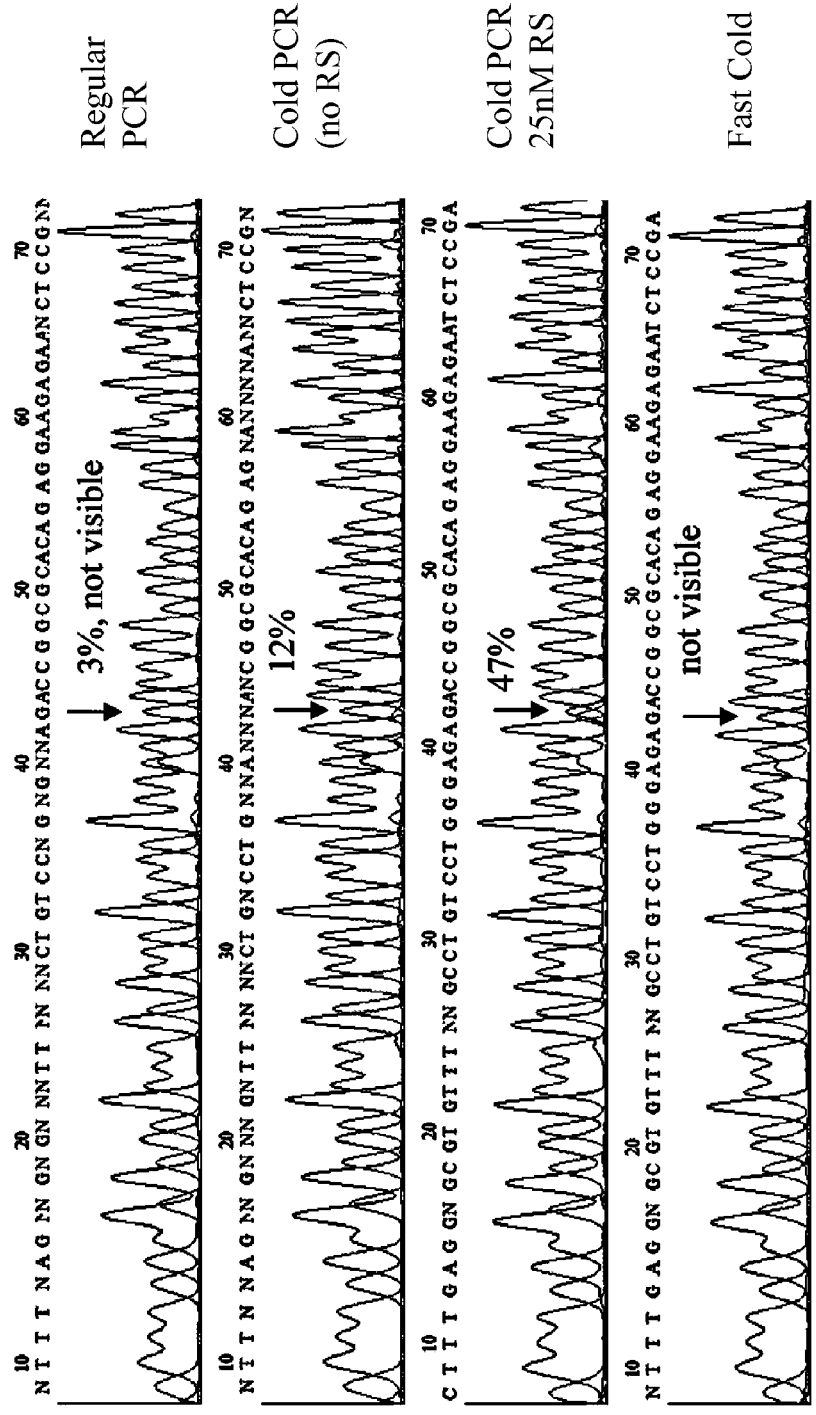
FIG. 5 displays Sanger sequencing data for the enrichment of HCC1008 mutant alleles from samples processed using regular PCR, full COLD-PCR without the use of a reference blocking sequence in the reaction mixture; full COLD-PCR with an excess of reference blocking sequence (RS) (60 bp) in the reaction mixture, and fast COLD-PCR, respectively.
Figure 6:
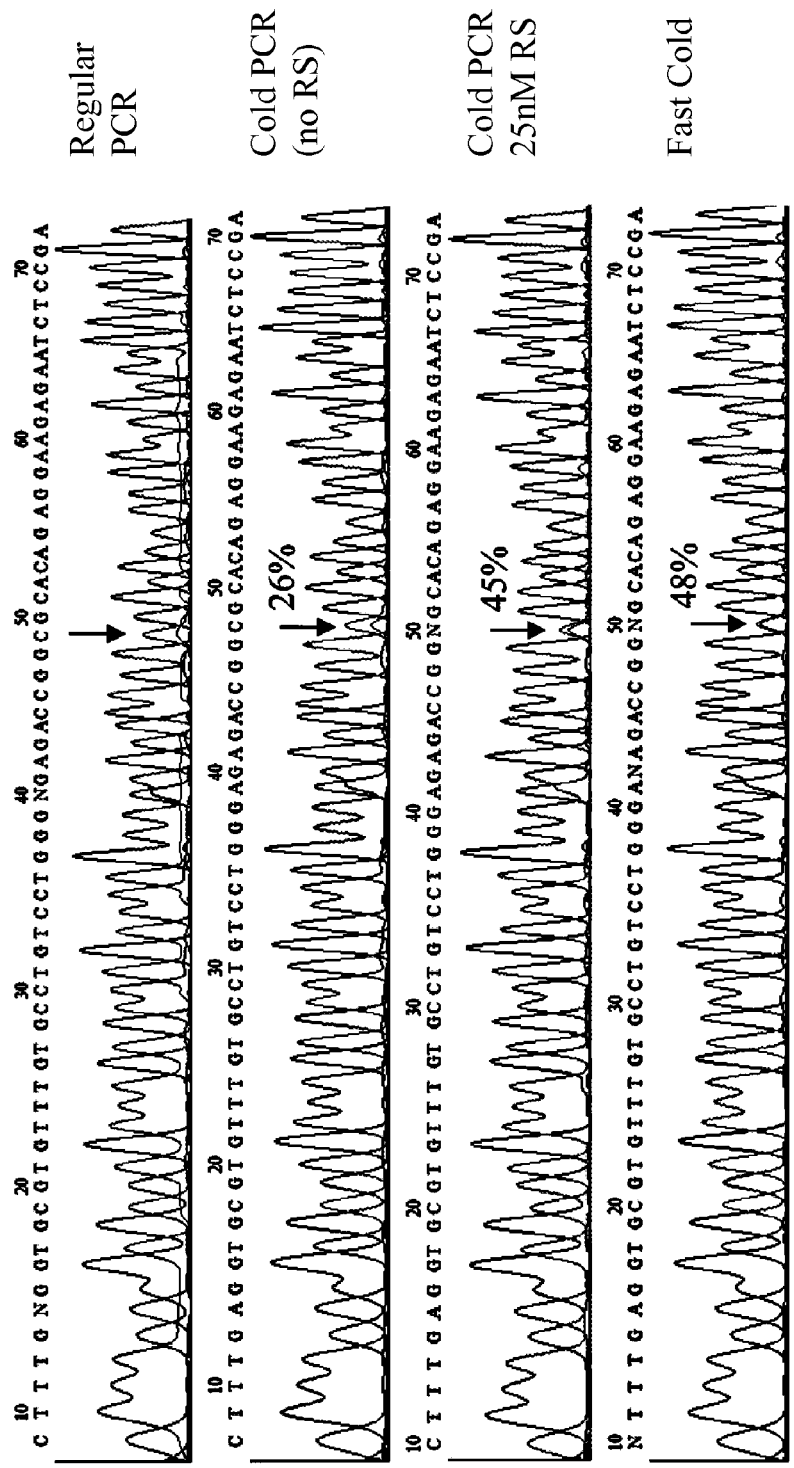
FIG. 6 displays Sanger sequencing data for the enrichment of HCC2218 mutant alleles from samples processed using regular PCR, full COLD-PCR without the use of a reference blocking sequence in the reaction mixture; full COLD-PCR with an excess of reference blocking sequence (RS) in the reaction mixture, and fast COLD-PCR, respectively.
Figure 7:
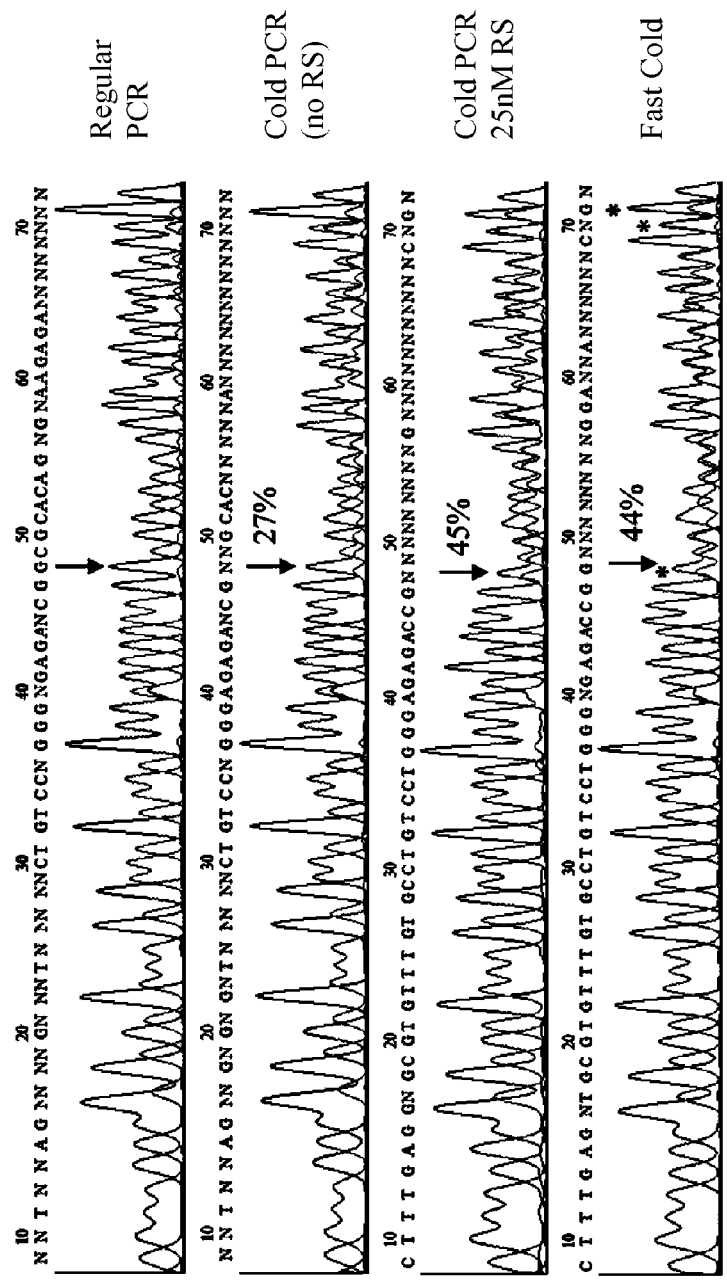
FIG. 7 displays Sanger sequencing data for the enrichment of TL92 mutant alleles (1 bp G del) from samples processed using regular PCR, full COLD-PCR without the use of a reference blocking sequence in the reaction mixture; full COLD-PCR with an excess of reference blocking sequence (RS) in the reaction mixture, and fast COLD-PCR, respectively.

FIG. 4 illustrates that enrichment via modified full COLD-PCR (25 nM RBS) is robust (an increase from 3% to 37%) for a circumstance in which the mutation increases the melting temperature. The mutation is not detectable when using fast COLD-PCR and conventional PCR in FIG. 4. FIG. 5 similarly illustrates that enrichment via modified full COLD-PCR (25 nM RBS) is robust (an increase from 3% to 47%) for a circumstance in which the mutation does not effect melting temperature. Again, the mutation is not detectable when using fast COLD-PCR and conventional PCR in FIG. 5. FIG. 6 also illustrates that enrichment via modified full COLD-PCR (25 nM RBS) is robust (an increase from 3% to 45%) for a circumstance in which the mutation reduces melting temperature. In FIG. 6, enrichment via fast COLD-PCR is robust as well (i.e., due to the reduced melting temperature). Again, in FIG. 6, the mutation is not detectable when using conventional PCR. FIG. 7 illustrates the results for a temperature reducing deletion. Enrichment via modified full COLD-PCR (25 nM RBS) is robust (an increase from 3% to 45%) as is enrichment via fast COLD-PCR. Again, the mutation is not detectable when using conventional PCR.

Figure 8:
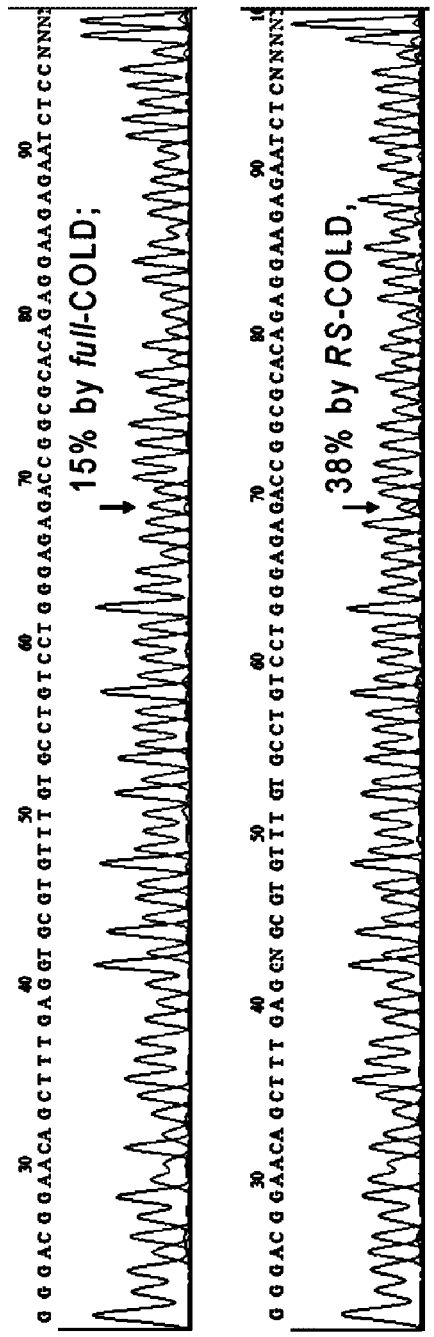
FIG. 8 displays Sanger sequencing data for the enrichment of HCC1008 mutant alleles from samples processed using full COLD-PCR with the use of a 90 bp reference blocking sequence (RS).

FIG. 8 displays Sanger sequencing data for the enrichment of HCC1008 mutant alleles from samples processed using RBS90, and illustrates that enrichment with modified full COLD-PCR in the presence of the 90 bp reference blocking sequence is robust (an increase from 3% to 38%). Comparing the results in FIG. 5, which displays Sanger sequencing data for the enrichment of HCC1008 mutant alleles from samples processed using RBS60, to the results in FIG. 8 confirms that the method of the present invention is robust with reference blocking sequences of different lengths. In all cases and for all mutations studied thus far, modified full COLD-PCR (in presence of RBS) appears to have the best performance, in that it enriches all types of mutations ($T_m$ increasing, retaining or decreasing mutations), in a short reaction time, and with better enrichment than Full-COLD-PCR (no RBS).

I claim:

1. A method for enriching a target sequence in an amplification mixture, said method comprising:
   a) preparing an amplification reaction mixture comprising at least the following constituents:
   a nucleic acid sample comprising a reference sequence and also suspected of having one or more target sequences that are at least 50% homologous to said reference sequence and are also amplifiable by the same primer pair as said reference sequence, and a molar excess of reference blocking sequence relative to the amount of reference sequence, the reference sequence being fully complementary with at least a portion of the sequence of one of the strands of the reference sequence between its primer pair binding sites;
   b) increasing the temperature of the reaction mixture suspected of having said target sequence to a first denaturing temperature that is above the melting temperature ($T_m$) of the double stranded reference sequence and above the melting temperature ($T_m$) of the double stranded target sequence so as to form denatured reference strands and denatured target strands;
   c) reducing the temperature of the reaction mixture so as to permit formation of duplexes of the reference blocking sequence and the complementary reference strand and heteroduplexes of the reference blocking sequence and target strands;
   d) increasing the temperature of said reaction mixture to a critical temperature ($T_c$) sufficient to permit preferential denaturation of said heteroduplexes of the reference blocking sequence and target strands in preference to denaturation of the duplexes of the reference blocking sequence and reference strands;
   e) reducing the temperature of the reaction mixture so as to permit said primer pair to anneal to denatured target strands and any denatured reference strands in the reaction mixture;
   f) extending said primers annealed to the denatured target strands and denatured reference strands in the reaction mixture; and
   g) repeating steps b) through f) in order for two or more cycles so as to enrich said target sequence relative to said reference sequence.

2. The method of claim 1 wherein a 3'-end of the reference blocking sequence is blocked to inhibit extension.

3. The method of claim wherein the 5'-end on the reference blocking sequence strands comprises a nucleotide that prevents 5' to 3' exonucleolysis by Taq DNA polymerases.

4. The method of claim 1 wherein the reference blocking sequence is provided in step a) as a single-stranded nucleic acid reference blocking sequence.

5. The method of claim 1 wherein the reference blocking sequence is provided in step a) as double-stranded nucleic acid reference blocking sequence which denatures to form single-stranded reference blocking sequences in step b) when the reaction mixture is subject to the first denaturing; temperature.

6. The method of claim 1 wherein the reference blocking sequence is one of single-stranded DNA, RNA, peptide nucleic acid or locked nucleic acid.

7. The method of claim 1 wherein the reference blocking sequence is a chimera between single-stranded DNA, RNA, peptide nucleic acid or locked nucleic acid or another modified nucleotide.

8. The method of claim 7 wherein the position of the peptide nucleic acid or locked nucleic acid on the chimera sequence are selected to match positions where mutations are suspected to be present, thereby maximizing the difference between the temperature needed to denature heteroduplexes of the reference blocking sequence and target strands and the temperature needed to denature heteroduplexes of the reference blocking sequence and the complementary reference strand.

9. The method of claim 1 wherein the reference blocking sequence is fully complementary with one of the strands of the reference sequence between its primer binding sites, or overlapping at either end the primer binding sites.

10. The method of claim 1 wherein the reference blocking sequence is equal to or shorter than the reference sequence.

11. The method of claim wherein the cooling step c) is less than one minute.

12. The method of claim 1 wherein the reference blocking sequence is present in the reaction mixture at a concentration level of about 25 nM.

13. The method of clam 1 wherein the melting temperature of the double-stranded target sequence is greater than or equal to the melting temperature of the double-stranded reference sequence, and the first denaturing temperature is above the melting temperature of the double-stranded target sequence.

14. The method of claim 1 wherein said reference and target sequences are first amplified by subjecting the nucleic acid sample to PCR and then subjecting at least a portion of the amplified nucleic acid sample to the enrichment method of claim 1.

15. The method of claim 1 wherein said target sequence comprises a homozygous mutation.

16. The method of claim 1 wherein said target sequence is differentially methylated from the reference sequence, and prior to implementing the method of claim 1 on the nucleic acid sample, the nucleic acid sample is treated with sodium bisulfite.

17. The method of claim 1 wherein said reference and target sequences comprise at least 25 base pairs.

18. The method of claim 1 thither comprising the step of analyzing said reaction mixture with enriched target sequence using one or more of the methods selected from the group consisting of: MALDI-TOF, HR-Melting, Di-deoxy-sequencing, Single-molecule sequencing, pyrosequencing, Second generation high-throughput sequencing, SSCP, RFLP, dHPLC, CCM, digital PCR and quantitative-PCR.

19. The method of claim 1 wherein said $T_c$ is applied for 1 second-60 seconds.

20. The method of claim 1 wherein said reaction mixture contains a nucleic acid detection dye.

21. The method of claim 14 wherein said method is performed in a real-time PCR device.

22. The method of claim 1 wherein said method is performed under a real time reaction condition utilizing a labeled probe.

23. The method of claim 1 wherein the primer extension step f) comprises increasing the temperature of the reaction mixture in order to promote extension of the annealed primers.

* * * * *